United States Patent
Balestrini et al.

(10) Patent No.: US 10,597,577 B2
(45) Date of Patent: Mar. 24, 2020

(54) ESTERAMIDES AND SUBTERRANEAN TREATMENT FLUIDS CONTAINING SAID ESTERAMIDES

(71) Applicant: LAMBERTI SPA, Albizzate (IT)

(72) Inventors: Andrea Balestrini, Sugar Land, TX (US); Quenton Christopher Villareal, Rosenberg, TX (US); Sama Nazar Makiah, Richmond, TX (US); Giovanni Floridi, Novara (IT); Giuseppe Li Bassi, Gavirate (IT)

(73) Assignee: Lamberti SPA, Albizzate (VA) (IT)

( * ) Notice: Subject to any disclaimer, the term of this patent is extended or adjusted under 35 U.S.C. 154(b) by 164 days.

(21) Appl. No.: 15/575,766

(22) PCT Filed: May 25, 2016

(86) PCT No.: PCT/EP2016/061760
§ 371 (c)(1),
(2) Date: Nov. 20, 2017

(87) PCT Pub. No.: WO2016/189019
PCT Pub. Date: Dec. 1, 2016

(65) Prior Publication Data
US 2018/0118994 A1    May 3, 2018

(30) Foreign Application Priority Data
May 26, 2015    (IT) .............. UB2015A0865

(51) Int. Cl.
| C09K 8/36 | (2006.01) |
|---|---|
| C04B 28/02 | (2006.01) |
| C09K 8/467 | (2006.01) |
| C04B 24/28 | (2006.01) |
| C07C 231/14 | (2006.01) |
| C07C 235/74 | (2006.01) |
| C09K 8/64 | (2006.01) |
| C09K 8/82 | (2006.01) |
| C09K 8/42 | (2006.01) |
| C09K 8/60 | (2006.01) |

(52) U.S. Cl.
CPC .............. *C09K 8/36* (2013.01); *C04B 24/287* (2013.01); *C04B 28/02* (2013.01); *C07C 231/14* (2013.01); *C07C 235/74* (2013.01); *C09K 8/467* (2013.01); *C09K 8/42* (2013.01); *C09K 8/602* (2013.01); *C09K 8/64* (2013.01); *C09K 8/82* (2013.01)

(58) Field of Classification Search
CPC ..... C04B 24/287; C04B 28/02; C07C 231/14; C07C 235/74; C09K 8/36; C09K 8/42; C09K 8/467; C09K 8/602; C09K 8/64; C09K 8/82
See application file for complete search history.

(56) References Cited

U.S. PATENT DOCUMENTS

| 2,946,746 A | 7/1960 | Keller, Jr. |
|---|---|---|
| 4,575,428 A | 3/1986 | Clapper et al. |
| 4,658,036 A | 4/1987 | Schilling |
| 6,004,914 A | 12/1999 | Perella et al. |
| 2003/0162668 A1 | 8/2003 | Kirsner et al. |
| 2007/0167333 A1 | 7/2007 | Hurd et al. |
| 2011/0306523 A1 | 12/2011 | Yu et al. |
| 2014/0121135 A1 | 5/2014 | Gamage et al. |
| 2015/0368539 A1* | 12/2015 | Tour .................. G01V 3/24 340/854.3 |

FOREIGN PATENT DOCUMENTS

WO    8911516 A1    11/1989

* cited by examiner

*Primary Examiner* — Alicia Bland
(74) *Attorney, Agent, or Firm* — Elisabeth Rather Healy; Vorys, Sater, Seymour and Pease LLP

(57) ABSTRACT

Water-in-oil subterranean treatment fluids with improved stability and environmental compatibility comprise esteramides as emulsion stabilizer.

21 Claims, No Drawings

ESTERAMIDES AND SUBTERRANEAN TREATMENT FLUIDS CONTAINING SAID ESTERAMIDES

FIELD OF THE INVENTION

The present invention relates to water-in-oil subterranean treatment fluids with improved stability and environmental compatibility, and to their use in subterranean treatments; more particularly, the described treatment fluids comprise esteramides as emulsion stabilizers. Subterranean treatments fluids are meant to include drilling and completion fluids, as well as other fluids used in subterranean operations such as stimulation fluids, etc.

STATE OF THE ART

Various types of subterranean treatment fluids, such as drilling fluids, are used in operations related to the development, completion, and production of natural hydrocarbon reservoirs.

These fluids may be classified according to their fluid base. Water base fluids contain solid particles suspended in water or brine. Alternatively, oil based fluids contain solid particles suspended in an oil continuous phase or, possibly, in water or brine emulsified within a oil (water-in-oil emulsions).

Water-in-oil emulsions have the oil phase as the continuous phase and a fluid at least partially immiscible in the oil phase (usually an aqueous-based fluid) as the discontinuous phase.

Water-in-oil emulsions may be also referred to as invert emulsions. Invert emulsions are preferred as drilling fluids when the formation is remarkably sensitive to contact with water and they usually have a better thermal resistance and guarantee better lubrication of the drill strings and downhole tools, thinner filter cake formation and improved hole stability. Emulsions are generally stabilized by addition of one or more emulsion stabilizing agents, also referred to as emulsifiers, which prevent the droplets coalescence, phase separations and the reduction of their performances.

When used in subterranean applications, emulsions undergo exceptional mechanical and thermal stress, and therefore stability is an especially critical aspect of their formulation.

The emulsifiers that are traditionally used in subterranean treatment fluids have surfactant-character, comprising a hydrophobic portion and a hydrophilic portion.

Examples of these emulsifiers are (poly)amides that are obtained from the condensation of fatty acids/carboxylic acids with (poly)amines, which show remarkable emulsifying and dispersing properties and are useful in various applications where invert emulsions are formed.

For example, U.S. Pat. No. 2,946,746 describes water-in-oil type emulsions comprising a polyamide emulsifying agent which may be prepared by reacting a polyethylene polyamine with a monobasic fatty acid in sufficient quantity to react with all of the amino groups of the polyethylene polyamine, thereby converting them to fatty acid amide groups.

U.S. Pat. No. 4,658,036 discloses a process for the preparation of invert emulsifiers useful for oil-base drilling muds. The emulsifiers are prepared by reacting tall oil fatty acids with acrylic acid, maleic anhydride or fumaric acid. The product of this reaction is reacted with diethylene triamine and at least one tall oil fatty acid to give the invert emulsifier.

WO 89/11516 relates to an oil-based well-working fluid comprising: a) an emulsifier comprising the reaction product of i) one or two moles of an amide-amine or a hydroxyalkyl amide with ii) one to five moles of a dicarboxylic acid or an acid anhydride; b) a hydrocarbon drilling oil; and c) a sodium, calcium or magnesium brine.

US 2003/162668 describes a method and a product which provides emulsion stability and filtration control to invert emulsion drilling fluids. The product comprises a blend of a carboxylic acid terminated polyamide and a mixture produced by the Diels-Alder reaction of dienophiles.

US 2011/0306523 relates to emulsifiers for oil-based drilling fluids based on the polyamides derived from fatty acids/carboxylic acids and optionally alkoxylated polyamines.

US 2014/121135 discloses an invert emulsion comprising an aqueous fluid, an oleaginous fluid and an emulsifier composition, wherein the emulsifier composition comprises: from 25 to 100 wt % of an emulsifier, which can comprise a carboxylic acid-terminated polyamide. This may be a product of a condensation reaction between a fatty acid, a polyamine and an acid anhydride or a polycarboxylic acid.

Unfortunately, many of these emulsifier are highly viscous liquids, almost solid, especially under low temperature conditions, so they must be formulated/diluted with an appropriate solvent to be manageable. This forces the operators to choose a fluid based on the compatibility with the solvent used in the liquid emulsifier formulations, or vice versa.

In order to avoid this problem, emulsifiers in the form of powder have been developed. For example, US 2007/167333 describes a spray dried emulsifier comprising a a carboxylic acid terminated fatty amide which is prepared by reacting a fatty acid amine condensate with a polycarboxylic acid or a carboxylic acid anhydride.

However, it can be difficult to disperse/solubilize efficiently and quickly these solid emulsifiers into in the oil phase and/or the aqueous phase of the invert subterranean treatment fluids, which usually contain high amount of undissolved solids.

For these reasons, there is still a industry-wide interest in, and on-going need for, more efficient and concentrated subterranean treatment fluid additives that can be easily manipulated and for subterranean treatment fluids which can be formulated with minimal or fewer additives than with common prior art fluids.

It has now surprisingly been found that esteramides, obtained by condensation reaction between $C_6$-$C_{30}$ aliphatic monocarboxylic acids, polyamines and polycarboxylic acid esters, are liquid with a pour point at temperatures below zero ° C. without the addition of any solvent. Thus, they may be manipulated and transported in a highly (more than 90% by weight) active state, which reduces the need of inventory products containing different solvents for compatibility with the treatment fluid. Moreover, this allows to further eliminate the need for transporting large amounts of inert and useless materials.

These esteramides can be prepared by reacting the monocarboxylic acids and polyamines in such proportion as to create a "partial amide" intermediate; the remaining amine sites are reacted with a polycarboxylic acid ester to produce the esteramides, i.e. amides which contain residual ester groups.

The esteramides so obtained show excellent properties as emulsifier when they are used in invert subterranean treatment fluids, being able to guarantee optimal stability of the fluids in the presence of solid components/contaminants and even at the high temperatures which can be found in the subterranean treatments, for examples in oil well drilling.

DESCRIPTION OF THE INVENTION

One of the object of the present invention are esteramides obtained by preparing in a first step an amide by reaction of one mole of a polyamine having n primary or secondary amino groups, wherein n is an integer ranging from 2 to 4, with from 1 to n−1 moles of a saturated or unsaturated $C_6$-$C_{30}$ aliphatic monocarboxylic acid; and, in a second step, reacting the remaining primary or secondary amino groups with from 0.4 to 1.3 moles, for each remaining amino group, of a diester of a $C_2$-$C_{10}$ dicarboxylic acid or of a di- or tri-ester of a tricarboxylic acid; characterized in that the esteramides have ester number higher than 12 $mg_{KOH}$/g, preferably higher than 25 $mg_{KOH}$/g, more preferably higher than 40 $mg_{KOH}$/g.

Further, according to the invention, there is provided a water-in-oil subterranean treatment fluid comprising: an oil phase, an aqueous phase and said esteramides as emulsion stabilizing agents.

In a further embodiment, the present invention provides a method of treating a subterranean formation that comprises: providing a water-in-oil subterranean treatment fluid containing an oil phase, an aqueous phase and said esteramides as the emulsion stabilizing agents and placing this fluid into the subterranean formation at a pressure to treat the formation.

The features and advantages of the present invention will be readily apparent to those skilled in the art upon reading of the description of the preferred embodiments which follows.

DETAILED DESCRIPTION OF THE INVENTION

With the term "esteramides" we mean the product obtained by the above detailed process, i.e. by preparing in a first step an amide by reaction of one mole of a polyamine having n primary or secondary amino groups, wherein n is an integer ranging from 2 to 4, with from 1 to n−1 moles of a saturated or unsaturated $C_6$-$C_{30}$ aliphatic monocarboxylic acid; and, in a second step, reacting the remaining primary or secondary amino groups with from 0.4 to 1.3 moles, for each remaining amino group, of a diester of a $C_2$-$C_{10}$ dicarboxylic acid or of a di- or tri-ester of a tricarboxylic acid.

The ester number of the esteramides can be determined using the ASTM standard method D5558-95.

The amide which is obtained in the first step of the process for the preparation of the esteramides may actually be a mixture of amides.

In a preferred embodiment of the invention the polyamine has n primary or secondary amino groups, wherein n is 3 or 4. More preferably n is 3.

Suitable polyamines that may be used for the preparation of the esteramides of the invention include, for example, polyalkylene polyamines.

The polyalkylene polyamines that advantageously may be employed as a starting material include compounds having the formula I:

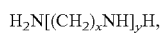  I where x is an integer ranging from 1 to 6 and y is an integer ranging from 1 to 3.

Preferably, the polyamine has formula I in which x is 2 and y is 2 or 3 and is therefore diethylene triamine or triethylene tetramine. More preferably, in formula I x is 2 and y is 2, i.e. the polyamine is diethylene triamine.

Other examples of suitable polyamines are polyethyleneimines with a average molecular weight of below about 200 dalton, which exhibit a low degree of branching.

Examples of $C_6$-$C_{30}$ aliphatic unsaturated monocarboxylic acids suitable for the present invention include both unsaturated and polyunsaturated aliphatic carboxylic acids with from 6 to 30 carbon atoms. Examples of these acids are palmitoleic acid, oleic acid, linoleic acid, linolenic acid, arachidonic acid, and the like.

Examples of $C_6$-$C_{30}$ aliphatic saturated monocarboxylic acids include decanoic acid, lauric acid, myristic acid, palmitic acid, stearic acid, behenic acid, and the like.

Mixtures of $C_6$-$C_{30}$ saturated and unsaturated aliphatic monocarboxylic acids can also be used.

Mixtures of monocarboxylic acid derived from natural oils, such as coconut oil, mustard seed oil, palm oil, olein, soy oil, canola oil, tall oil, sunflower oil, and mixture thereof, are particularly preferred.

In one embodiment of the invention, the $C_6$-$C_{30}$ monocarboxylic acid is a mixture of $C_6$-$C_{30}$ saturated and unsaturated aliphatic monocarboxylic acids comprising at least 50% by weight, preferably at least 70% by weight, of oleic acid.

Preferably, the monocarboxylic acid source is selected from tall oil, rape seed oil, mustard seed oil and mixtures thereof.

Tall oil is particularly preferred as the $C_6$-$C_{30}$ aliphatic saturated and unsaturated monocarboxylic acids source for use in the process for making the esteramides of the present invention.

The preparation of the amide may be carried out according to methods well known to those skilled in the art, by heating the polyamine and the monocarboxylic acid up to 250° C., preferably from 140 to 180° C., either or not, in a suitable hydrocarbon solvent such as toluene or xylene and azeotroping off the formed water, with or without catalysts such as p-toluenesulphonic acid, zinc acetate, zirconium naphthenate or tetrabutyl titanate. The end-point of the reaction is considered to be reached when the acid number of the reaction mixture, determined by ASTM standard method D1980-87, is below 20 $mg_{KOH}$/g, preferably below 10 $mg_{KOH}$/g.

When the polyamine used is diethylene triamine, preferably, in the first step one mole of diethylene triamine is reacted with from 1.5 to 2.0 moles of acid.

More generally, preferably, in the first step one mole of polyamine is reacted with about n−1 moles of saturated or unsaturated $C_6$-$C_{30}$ aliphatic monocarboxylic acid.

The ester of $C_2$-$C_{10}$ di- or tri-carboxylic acid that can be reacted with the above-described amides to form the emulsifiers of the present invention is the ester of a $C_2$-$C_{10}$ di- or tri-carboxylic carboxylic acid, or possibly the corresponding anhydride, with a $C_1$-$C_8$, preferably $C_1$-$C_5$, linear or branched alcohol or with a monoalkyl ether of ethylene or propylene glycol, or with mixtures thereof; most advantageously, the ester does not contain acid groups, being a diester of a dicarboxylic acid or a triester of a tricarboxylic acid.

The di- or tri-carboxylic acid used to prepare the ester has preferably from 3 to 8 carbon atoms.

Examples of suitable $C_2$-$C_{10}$ di- or tri-carboxylic acids include succinic acid, malonic acid, (ethylenedioxy) diacetic acid, maleic acid, diglycolic acid, tartaric acid, tartronic acid and fumaric acid; citric acid, aconitic acid, citraconic acid, carboxymethyloxysuccinic acid and lactoxysuccinic acid; phthalic acid; and mixtures thereof.

Preferably, the $C_2$-$C_{10}$ di- or tri-carboxylic acid is fumaric acid, malonic acid, maleic acid or citric acid; or mixtures thereof.

$C_2$-$C_{10}$ dicarboxylic acids are preferred for the realization of the present invention.

Suitable $C_1$-$C_8$ linear or branched alcohols used to prepare the ester are methanol, ethanol, propanol, iso-propranol, n-butanol, iso-butanol, tert-butanol, pentanol, hexanol, 2-ethyl hexyl alcohol and the like. Preferred $C_1$-$C_8$ linear or branched alcohols are ethanol and isopropanol.

Monoalkyl ethers of ethylene or propylene glycols, wherein the alkyl group has from 1 to 4 carbon atoms, such as the cellosolves, can also be used to prepare the esters of $C_2$-$C_{10}$ di- or tri-carboxylic acid suitable for the realization of the present invention. Examples of these glycol monoalkyl ethers are ethylene glycol monomethyl ether, ethylene glycol monobutyl ether, diethylene glycol monomethyl ether, dipropylene glycol monomethyl ether, diethylene glycol monobutyl ether, etc.

In a particularly preferred embodiment the ester of $C_2$-$C_{10}$ di- or tri-carboxylic acid is chosen among diethyl maleate, diethyl fumarate, di(ethylene glycol monobutyl ether) maleate, di(diethylene glycol monobutyl ether) maleate and mixtures thereof.

The remaining primary or secondary amino groups of the amide and the di- or tri-carboxylic esters described above can be condensed at a temperature ranging from about 120° C. to about 250° C., preferably from about 140° C. to about 200° C., while the formed $C_1$-$C_8$ alcohol or the monoalkyl ether of ethylene or propylene glycol is distilled off. The end-point of the reaction is considered to be reached when the total amine value of the reaction mixture, determined by ASTM standard method D2074-12, is below 60 $mg_{KOH}/g$, preferably below 40 $mg_{KOH}/g$, more preferably below 20 $mg_{KOH}/g$.

Preferably, the remaining primary or secondary amino groups are reacted with from 0.4 to 1.0 moles, more preferably with about 1 mole, of ester of a $C_2$-$C_{10}$ di- or tri-carboxylic acid for each remaining amino group.

In a particularly preferred embodiment of the invention, the $C_1$-$C_8$ alcohol or monoalkyl ethers of ethylene or propylene glycol which are generated during the condensation of the ester of the di- or tricarboxylic acid with the amide, are removed from the final product. As a consequence, generally, the esteramides of the invention does not contain but traces of volatile organic compounds (VOC). Therefore, even if the esteramides could contain up to 10% by weight of the alcohols or of the monoalkyl glycol ethers, most preferably it only contains up to 2% by weight of these compounds, being still in liquid form at ambient temperature.

The water-in-oil subterranean treatment fluid of the present invention comprises an oil phase, an aqueous phase (a water based fluid that is at least partially immiscible with the oil phase), and from 0.5 to 5.0% weight/volume, preferably from 1.0 to 4.0% weight/volume, of the esteramide.

According to an advantageous embodiment of the present invention, the water-in-oil fluids do not comprise any additional emulsifier, except the esteramides.

The concentration of the oil phase in the water-in-oil fluid should be sufficient so to form an invert emulsion and may be less than about 90 percent in volume of the invert emulsion (vol. %).

In an embodiment, the amount of oil phase is from about 20 to about 85 vol. %, preferably from about 50 to about 85 vol. % based on the total volume of fluid the invert emulsion.

In another embodiment, inverse high internal phase ratio emulsions, i.e. systems possessing a larger volume of internal aqueous phase (>50% in volume), are preferred because of the significant reduction of the oil phase, with its associated costs and possible environmental concern for possible contamination and waste disposal.

The oil phase used in the invert emulsions of the present invention may comprise any oil-based fluid suitable for use in emulsions.

The oil phase may derive from a natural or synthetic source. Examples of suitable oil phase include, without limitation, diesel oils, paraffin oils, mineral oils, low toxicity mineral oils, olefins, esters, amides, amines, synthetic oils such as polyolefins, ethers, acetals, dialkylcarbonates, hydrocarbons and combinations thereof.

The preferred oil phases are paraffin oils, low toxicity mineral oils, diesel oils, mineral oils, polyolefins, olefins and mixtures thereof.

Factors determining which oil phase will be used in a particular application, include but are not limited to, its cost and performance characteristics, environmental compatibility, toxicological profile and availability.

The invert emulsions of the present invention also comprise an aqueous phase that is at least partially immiscible in the oil phase.

Suitable examples of aqueous phase include fresh water, sea water, salt water, brines (e.g. saturated salt waters), glycerin, glycols, polyglycol amines, polyols and derivatives thereof, that are partially immiscible in the oleaginous fluid, and combinations thereof.

Suitable brines may include heavy brines.

Heavy brines, for the purposes of this application, include brines with various salts at variable concentrations, that may be used to weight up a fluid; generally, the use of weighting agents is required to provide the desired density of the fluid.

Brines generally comprise water soluble salts.

Suitable water soluble salts are sodium chloride, calcium chloride, calcium bromide, zinc bromide, sodium formate, potassium formate, sodium acetate, potassium acetate, calcium acetate, ammonium acetate, ammonium chloride, ammonium bromide, sodium nitrate, potassium nitrate, ammonium nitrate, calcium nitrate, sodium carbonate, potassium carbonate, and mixtures thereof.

The aqueous phase is chosen taking into account several factors including cost, environmental and health safety profile, density, availability, and which oil phase has been chosen. Another factor that may be considered is the application of the subterranean treatment fluid.

For example, if the application needs an emulsion with a heavy weight, a zinc bromide brine may be chosen.

The subterranean treatment fluids of the invention may further comprise conventional additives including weighting agents, wetting agents, fluid loss agents, thickeners, thinning agents, lubricants, anti-oxidants, corrosion inhibitors, scale inhibitors, defoamers, biocides, pH modifiers, and the like.

Such fluids, in particular, also contain at least one filtrate reducer preferably chosen among gilsonite, organophilic lignite, organophilic tannins, synthetic polymers, polycarboxylic fatty acids and mixtures thereof.

When used in certain applications, the fluids may include particulates such as proppant or gravel.

The water-in-oil subterranean treatment fluids of the invention may be suitable for use in a variety of subterranean applications wherein water-in-oil emulsions are used; these applications include drilling, completion, stimulation operations (such as fracturing) and work-over, sand control treatments such as installing a gravel pack, spotting, cementing, maintenance and reactivation.

To better illustrate the invention, the following examples are reported to show the effect of the addition of different esteramides and of prior art carboxylic acid-terminated polyamides in exemplary water-in-oil drilling fluids.

EXAMPLES

Characterization Methods

The acid number was determined following the ASTM standard method ASTM-D1980-87.

The total amine value was determined following the ASTM standard method D2074-12.

The ester number was determined following the ASTM standard method D5558-95.

The Brookfield RV® viscosity was determined at 25° C. and 30 rpm using a Brookfield RV® viscosimeter.

The pour point was determined according to the ASTM standard method D97-12.

The drilling muds were evaluated according to the ISO standard method 10416-08, chapter 26.

Emulsifier Preparation

Example 1

Comparative 448.7 g of tall oil fatty acids (TOFA) were loaded in a 1000 ml glass reactor equipped with a Dean-Stark apparatus and a mechanical blade stirrer and heated to about 95° C. Then 80.8 g of diethylene triamine were added. The reaction mixture was further heated to 160° C. under nitrogen atmosphere and maintained at this temperature for 6 hours. At the end of the reaction, 27.6 g of water were recovered and the intermediate product had an acid number lower than 10 $mg_{KOH}/g$. Subsequently, the mass was cooled to about 82° C. and 76.9 g of maleic anhydride were slowly added. The reaction temperature was increased to 95° C. for 60 minutes. The final product had a total amine content below 20 $mg_{KOH}/g$ and was solid at room temperature.

Example 2

448.7 g of TOFA were loaded in a 1000 ml glass reactor equipped with a Dean-Stark apparatus and a mechanical blade stirrer and heated to about 95° C. Then 80.8 g of diethylene triamine were added. The reaction mixture was further heated to 160° C. under nitrogen atmosphere and maintained at this temperature for 6 hours. At the end of the reaction, 27.6 g of water were recovered and the intermediate product had an acid number below 10 $mg_{KOH}/g$. The mixture was cooled to about 115° C. and 135.1 g of diethyl maleate were slowly added. The reaction mass was heated to 150° C. always under nitrogen atmosphere and maintained at this temperature until about 35 g of ethanol were collected. The final product was liquid at room temperature, had a total amine content below 20 $mg_{KOH}/g$ and an ester number of 74 $mg_{KOH}/g$.

Example 3

228.8 g of TOFA were loaded in a 500 ml glass reactor equipped with a Dean-Stark apparatus and a mechanical blade stirrer and heated to about 95° C. Then 41.2 g of diethylene triamine were added. The reaction mixture was further heated to 160° C. under nitrogen atmosphere and maintained at this temperature for 6 hrs. At the end of the reaction, 13.8 g of water were recovered and the intermediate product had an acid number below 10 $mg_{KOH}/g$. The mixture was cooled to 115° C. and 57.6 g of dimethyl maleate were slowly added. The reaction mass was heated to 150° C. always under nitrogen atmosphere and maintained at this temperature until about 18 g of methanol were collected. The final product was liquid at room temperature, had a total amine content below 20 $mg_{KOH}/g$ and an ester number of 45.5 $mg_{KOH}/g$.

Example 4

228.8 g of TOFA were loaded in a 500 ml glass reactor equipped with a Dean-Stark apparatus and a mechanical blade stirrer and heated to about 95° C. Then 41.2 g of diethylene triamine were added. The reaction mixture was further heated to 160° C. under nitrogen atmosphere and maintained at this value for 6 hours. At the end of the reaction, 13.6 g of water were recovered and the intermediate product had an acid number below 10 $mg_{KOH}/g$. The mixture was cooled to 115° C. and 91.3 g of dibutyl maleate were slowly added. The reaction mass was heated to 160° C. always under nitrogen atmosphere and maintained at this temperature until about 27 g of butanol were collected. The final product was liquid at room temperature, had a total amine content below 20 $mg_{KOH}/g$ and an ester number of 77 $mg_{KOH}/g$.

Example 5

Comparative 424.8 g of TOFA were loaded in a 1000 ml glass reactor equipped with a Dean-Stark apparatus and a mechanical blade stirrer and heated to about 95° C. Then, 76.3 g of diethylene triamine were added. The reaction mixture was further heated to 160° C. under nitrogen atmosphere and maintained at this temperature for 6 hours. At the end of the reaction, 25.4 g of water were recovered and the intermediate product had an acid number below 10 $mg_{KOH}/g$. The mixture was cooled to about 135° C. and 142.1 g of citric acid were added over a period of one hour. The reaction mass was heated to 160° C. always under nitrogen atmosphere and maintained at this temperature until about 18 g of water were collected. The final product had a total amine content below 40 $mg_{KOH}/g$ and was solid at room temperature.

Example 6

277.8 g of TOFA were loaded in a 1000 ml glass reactor equipped with a Dean-Stark apparatus and a mechanical blade stirrer and heated to about 95° C. Then 66.6 g of diethylene triamine were added. The reaction mixture was further heated to 160° C. under nitrogen atmosphere and maintained at this temperature for 6 hours. At the end of the reaction, 16.5 g of water were recovered and the intermediate product had an acid number lower than 10 $mg_{KOH}g$.

The mixture was cooled to about 115° C. and 133.9 g of triethyl citrate were slowly added. The reaction mass was heated to 175° C. always under nitrogen atmosphere and maintained at this temperature until about 40 g of ethanol were recovered. The final product was liquid at room temperature, had a total amine content below 40 mg$_{KOH}$/g and an ester number of 77 mg$_{KOH}$g.

Example 7

Comparative 242.8 g of TOFA were loaded in a 500 ml glass reactor equipped with a Dean-Stark apparatus and a mechanical blade stirrer and heated to about 95° C. Then, 58.3 g of diethylene triamine were added. The reaction mass was further heated to about 230° C. under nitrogen atmosphere and maintained at this temperature for 3 hrs. At the end of the reaction, 21.5 g of water were recovered and the intermediate product had an acid number below 7 mg$_{KOH}$/g.

The mixture was cooled to about 82° C. and 38.8 g of maleic anhydride were slowly added. The reaction mass was slowly heated to about 150° C. under nitrogen atmosphere and maintained at this temperature for 2 hours. Then, the temperature was further increased to about 175° C. for another 2 hours, maintaining the nitrogen atmosphere. The final product had a total amine content below 60 mg$_{KOH}$/g and was solid at room temperature.

Example 8

242.8 g of TOFA were loaded in a 500 ml glass reactor equipped with a Dean-Stark apparatus and a mechanical blade stirrer and heated to about 95° C. Then, 58.3 g of diethylene triamine were added. The reaction mass was heated to 165° C. under nitrogen atmosphere and maintained at this temperature for 6 hrs. The temperature was further increased to 230° C. for other 3 hours, maintaining the nitrogen atmosphere. At the end of the reaction 20.0 g of water were recovered and the intermediate product had an acid number below 7 mg$_{KOH}$/g.

The mass was cooled to about 115° C. and 68.2 g of diethyl maleate were slowly added. Subsequently, the reaction mass was heated to about 175° C. always under nitrogen atmosphere and maintained at this temperature until about 20 g of ethanol were collected. The final product was liquid at room temperature, had a total amine content below 60 mg$_{KOH}$/g and an ester number of 61.2 mg$_{KOH}$/g.

Example 9

228.8 g of TOFA were loaded in a 500 ml glass reactor equipped with a Dean-Stark apparatus and a mechanical blade stirrer and heated to about 95° C. Then, 41.2 g of diethylene triamine were added. The reaction mass was further heated to 160° C. under nitrogen atmosphere and maintained at this temperature for 6 hours. At the end of the reaction 13.8 g of water were recovered and the intermediate product had an acid number below 10 mg$_{KOH}$/g.

The mixture was cooled to about 115° C. and 126.3 g of di(2-butoxyethyl) maleate were added. The reaction mass was again heated to 150° C. under nitrogen atmosphere and maintained at this temperature until the total amine content was below 20 mg$_{KOH}$/g. The final product was liquid at room temperature and had an ester number of 83 mg$_{KOH}$/g.

Example 10

The emulsifier of Example 10 was prepared with the same procedure and the same amount of reagents of Example 9, only di(2-butoxyethyl) fumarate instead of di(2-butoxyethyl) maleate was used. The final product was liquid at room temperature.

The Brookfield RVT® viscosity and the pour point of the emulsifiers of Examples 1-10 are reported in Table 1.

The esteramides of the invention are liquid at room temperature and show a viscosity which allows an easy on-field manageability. Moreover, they exhibit a pour point well below zero ° C. which guarantee the same manageability even in low temperature environments.

TABLE 1

|  | Brookfield Viscosity (mPa · s) | Pour Point (° C.) |
| --- | --- | --- |
| Example 1* | Solid | ND |
| Example 2 | 2,990 | −14.4 |
| Example 3 | 12,160 | −8.9 |
| Example 4 | 5,360 | −10.5 |
| Example 5* | Solid | ND |
| Example 6 | 34,000 | −7.7 |
| Example 7* | Solid | ND |
| Example 8 | 5,000 | −11.6 |
| Example 9 | 600 | −20 |
| Example 10 | 674 | −10 |

*Comparative
ND = Not determined

Performance Test

The emulsifying performances of the esteramides of the invention were evaluated on exemplary drilling fluids.

350 ml of drilling muds were prepared by means of a Hamilton Beach Mixer according to the formulations described in Table 2.

The carboxylic acid-terminated polyamides of comparative Examples 1 and 5 were diluted with synthetic hydrocarbon solvent to a final concentration of active matter of 60% by weight.

For the preparation of the muds, the following commercial products were used:

EMULAM V-PLUS a organobentonite, commercialized by Lamberti USA.

ECOTROL RD a fluid loss reducer, commercialized by MI-SWACO, USA.

For the evaluation of the muds, the rheological properties, the electrical stability (ES) and the HTHP filtrate volume were determined after hot rolling for sixteen hours at 120° C. (250° F.) according to ISO 10416, par. 26.8. The determination conditions are described in ISO 10416 par. 26.10.

The results are reported in Table 3.

TABLE 2

|  | MUD 1* | MUD 2 | MUD 3 | MUD 4 | MUD 5 | MUD 6 | MUD 7 | MUD 8* |
| --- | --- | --- | --- | --- | --- | --- | --- | --- |
| Diesel | 179 | 179 | 179 | 179 | 179 | 179 | 179 | 179 |
| EMULAM V-PLUS | 5 | 5 | 5 | 5 | 5 | 5 | 5 | 5 |
| Lime | 6 | 6 | 6 | 6 | 6 | 6 | 6 | 6 |

TABLE 2-continued

|  | MUD 1* | MUD 2 | MUD 3 | MUD 4 | MUD 5 | MUD 6 | MUD 7 | MUD 8* |
|---|---|---|---|---|---|---|---|---|
| Oxidized Tall Oil | 0.5 | 0.5 | 0.5 | 0.5 | 0.5 | 0.5 | 0.5 | 0.5 |
| Example 1* | 10 | — | — | — | — | — | — | — |
| Example 2 | — | 6 | — | — | — | — | — | — |
| Example 3 | — | — | 6 | — | — | — | — | — |
| Example 4 | — | — | — | 6 | — | — | — | — |
| Example 8 | — | — | — | — | 6 | — | — | — |
| Example 9 | — | — | — | — | — | 7 | — | — |
| Example 10 | — | — | — | — | — | — | 7.25 | — |
| Example 5* | — | — | — | — | — | — | — | 10 |
| ECOTROL RD | 0.5 | 0.5 | 0.5 | 0.5 | 0.5 | 0.5 | 0.5 | 0.5 |
| 25% CaCl2 brine | 71 | 71 | 71 | 71 | 71 | 71 | 71 | 71 |
| Barite | 280 | 280 | 280 | 280 | 280 | 280 | 280 | 280 |

*Comparative

TABLE 3

|  |  | MUD 1* | MUD 2 | MUD 3 | MUD 4 | MUD 5 | MUD 6 | MUD 7 | MUD 8* |
|---|---|---|---|---|---|---|---|---|---|
| Rheology 600 |  | 38 | 41 | 40 | 43 | 39 | 44 | 35 | 47 |
| 300 |  | 22 | 24 | 25 | 26 | 22 | 28 | 20 | 27 |
| 200 |  | 15 | 18 | 17 | 19 | 15 | 21 | 14 | 20 |
| 100 |  | 9 | 11 | 11 | 13 | 9 | 14 | 8 | 12 |
| 6 |  | 2 | 4 | 4 | 4 | 2 | 5 | 3 | 4 |
| 3 |  | 1 | 3 | 3 | 3 | 1 | 4 | 2 | 3 |
| 10 sec Gel | lb/100 ft$^2$** | 2 | 3 | 4 | 4 | 2 | 5 | 2 | 4 |
| 10 min Gel | lb/100 ft$^2$** | 2 | 3 | 4 | 4 | 3 | 5 | 2 | 4 |
| PV | mPa·s | 16 | 17 | 15 | 17 | 17 | 16 | 15 | 20 |
| YP | lb/100 ft$^2$** | 6 | 7 | 10 | 9 | 5 | 12 | 5 | 7 |
| ES | Volt | 1399 | 776 | 1999 | 1999 | 1999 | 1999 | 1999 | 1999 |
| HTHP Filtr. Vol. | Oil ml | 2.2 | 1 | 4 | 2 | 9 | 2 | 12 | 6.2 |
|  | Water ml | 0 | 0 | 0 | 0 | 0 | 0 | 0 | 0 |

*Comparative
**1 lb/100 ft$^2$ = 0.479 Pa

The muds prepared with the emulsifier of the invention showed good rheological characteristic, also after the thermal treatment, comparable with those of the emulsifiers of the prior art. Moreover they showed low fluid loss and no water separation in the HTHP filtrates. The good performances of the emulsifiers of the inventions were also demonstrated by the high electrical stability values.

The invention claimed is:

1. A process for preparing an esteramide comprising:
reacting a polyamine having a total of n primary and/or secondary amino groups with a saturated or unsaturated $C_6$-$C_{30}$ aliphatic monocarboxylic acid, at a molar ratio of polyamine to saturated or unsaturated $C_6$-$C_{30}$ aliphatic monocarboxylic acid from 1:1 to about 1:n–1, wherein n is an integer ranging from 2 to 4, to form an amide; and
reacting the remaining polyamine primary or secondary amino groups with a diester of a $C_2$-$C_{10}$ dicarboxylic acid or with a di- or tri-ester of a tricarboxylic acid, at a molar ratio of from 0.4 to 1.3 moles of the diester of a $C_2$-$C_{10}$ dicarboxylic acid or of the di- or tri-ester of a tricarboxylic acid per each remaining amino group;
wherein the esteramide has an ester number higher than 12 mg$_{KOH}$/g.

2. The process of claim 1 wherein the esteramide has an ester number higher than 25 mg$_{KOH}$/g.

3. The process of claim 1 wherein the polyamine is a polyalkylene polyamine having formula I:

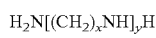

$$H_2N[(CH_2)_xNH]_yH \qquad I$$

where x is an integer ranging from 1 to 6 and y is an integer ranging from 1 to 3.

4. The process of claim 3 wherein, in formula I, x is 2 and y is 2 or 3.

5. The process of claim 4 wherein, in formula I, y is 2.

6. The process of claim 5 wherein, in the reacting a polyamine having a total of n primary and/or secondary amino groups with a saturated or unsaturated $C_6$-$C_{30}$ aliphatic monocarboxylic acid, the molar ratio of polyamine to saturated or unsaturated $C_6$-$C_{30}$ aliphatic monocarboxylic acid is from 1:1.5 to 1:2.0.

7. The process of claim 1 wherein the saturated or unsaturated $C_6$-$C_{30}$ aliphatic monocarboxylic acid is a mixture of $C_6$-$C_{30}$ saturated or unsaturated aliphatic monocarboxylic acids derived from a natural oil.

8. The process of claim of claim 7 wherein the natural oil is tall oil.

9. The process of claim 1 wherein the ester of a $C_2$-$C_{10}$ di- or tri-carboxylic acid is the ester of a $C_2$-$C_{10}$ di- or tri-carboxylic acid, or the corresponding anhydride, with a $C_1$-$C_8$ linear or branched alcohol or with a monoalkyl ether of ethylene or propylene glycol, or a mixture thereof.

10. The process of claim 9, wherein the ester is selected from the group consisting of diethyl maleate, diethyl fumarate, di(ethylene glycol monobutyl ether) maleate, di(diethylene glycol monobutyl ether) maleate and mixtures thereof.

11. An esteramide Prepare using a process comprising:
reacting a polyamine having a total of n primary and/or secondary amino groups with a saturated or unsaturated $C_6$-$C_{30}$ aliphatic monocarboxylic acid, at a molar ratio of polyamine to saturated or unsaturated $C_6$-$C_{30}$ aliphatic monocarboxylic acid from 1:1 to about 1:n−1, wherein n is an integer ranging from 2 to 4, to form an amide; and reacting the remaining polyamine primary or secondary amino groups with a diester of a $C_2$-$C_{10}$ dicarboxylic acid or with a di- or tri-ester of a tricarboxylic acid, at a molar ratio of from 0.4 to 1.3 moles of the diester of a $C_2$-$C_{10}$ dicarboxylic acid or of the di- or tri-ester of a tricarboxylic acid per each remaining amino group;

wherein the esteramide has an ester number higher than 12 $mg_{KOH}/g$.

12. The esteramide of claim 11 wherein the esteramide has an ester number higher than 25 $mg_{KOH}/g$.

13. The esteramide of claim 11 wherein the polyamine is a polyalkylene polyamine having formula I:

I where x is an integer ranging from 1 to 6 and y is an integer ranging from 1 to 3.

14. The esteramide of claim 13 wherein, in formula I, x is 2 and y is 2 or 3.

15. The esteramide of claim 14 wherein, in formula I, y is 2.

16. The esteramide of claim 15 wherein, in the reacting a polyamine having a total of n primary and/or secondary amino groups with a saturated or unsaturated $C_6$-$C_{30}$ aliphatic monocarboxylic acid, the molar ratio of polyamine to saturated or unsaturated $C_6$-$C_{30}$ aliphatic monocarboxylic acid is from 1:1.5 to 1:2.0.

17. The esteramide of claim 11 wherein the saturated or unsaturated $C_6$-$C_{30}$ aliphatic monocarboxylic acid is a mixture of $C_6$-$C_{30}$ saturated or unsaturated aliphatic monocarboxylic acids derived from a natural oil.

18. The esteramide of claim of claim 17 wherein the natural oil is tall oil.

19. The esteramide of claim 11 wherein the ester of a $C_2$-$C_{10}$ di- or tri-carboxylic acid is the ester of a $C_2$-$C_{10}$ di- or tri-carboxylic acid, or the corresponding anhydride, with a $C_1$-$C_8$ linear or branched alcohol or with a monoalkyl ether of ethylene or propylene glycol, or a mixture thereof.

20. The esteramide of claim 19, wherein the ester is selected from the group consisting of diethyl maleate, diethyl fumarate, di(ethylene glycol monobutyl ether) maleate, di(diethylene glycol monobutyl ether) maleate and mixtures thereof.

21. A water-in-oil subterranean treatment fluid comprising an aqueous phase, an oil phase and from 0.5 to 5.0% weight/volume of the esteramide of claim 11.

* * * * *